United States Patent [19]

Kehne et al.

[11] Patent Number: 4,652,666
[45] Date of Patent: Mar. 24, 1987

[54] α-ACYLOXIMINO-ALKANE-PHOSPHONIC (AND -PHOSPHINIC) ACID ESTERS

[75] Inventors: Heinz Kehne, Hofheim am Taunus; Hilmar Mildenberger, Kelkheim; Klaus Bauer, Rodgau; Hermann Bieringer, Eppstein, all of Fed. Rep. of Germany

[73] Assignee: Hoechst Aktiengesellschaft, Frankfurt am Main, Fed. Rep. of Germany

[21] Appl. No.: 756,352

[22] Filed: Jul. 18, 1985

[30] Foreign Application Priority Data

Jul. 20, 1984 [DE] Fed. Rep. of Germany ....... 3426718

[51] Int. Cl.⁴ .......................... C07F 9/40; C07F 9/32; A01N 57/06
[52] U.S. Cl. ......................................... 558/175; 71/86
[58] Field of Search ................................. 558/172, 175

[56] References Cited

FOREIGN PATENT DOCUMENTS

| | | |
|---|---|---|
| 86936 | 8/1983 | European Pat. Off. ............ 558/175 |
| 2504319 | 8/1975 | Fed. Rep. of Germany . |
| 2553442 | 6/1977 | Fed. Rep. of Germany . |
| 2808317 | 9/1978 | Fed. Rep. of Germany . |
| 1207788 | 10/1977 | United Kingdom . |

*Primary Examiner*—Anton H. Sutto
*Attorney, Agent, or Firm*—Curtis, Morris & Safford

[57] ABSTRACT

The novel compounds of the formula I

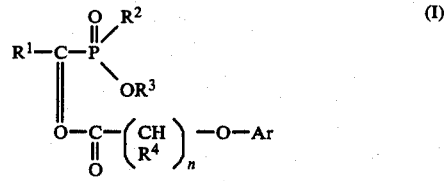

in which
$R^1$ denotes (subst.) alkyl, (subst.) alkenyl, (subst.) alkinyl, (subst.) cycloalkyl, phenyl, naphthyl or alkoxycarbonyl, $R^2$ denotes alkyl, alkoxy or phenyl, $R^3$ denotes alkyl, $R^4$ denotes H or alkyl, Ar denotes (subst.) phenyl, (subst.) naphthyl or (subst.) quinolyl and n denotes 1, 2, 3 or 4, have interesting safener properties, i.e. they reduce the phytotoxic side effects of herbicides.

3 Claims, No Drawings

α-ACYLOXIMINO-ALKANE-PHOSPHONIC (AND -PHOSPHINIC) ACID ESTERS

The present invention relates to novel α-acyloximinoalkane-phosphonic (and -phosphinic) acid esters of the formula I $$R^1-\underset{\underset{\underset{O}{\overset{|}{C}}-\underset{R^4}{\overset{|}{C}H}}{\overset{|}{O}}}{\overset{N}{\overset{||}{C}}}-P\overset{\overset{O}{\overset{||}{\diagup}}R^2}{\diagdown OR^3} \quad (I)$$

in which

R$^1$ denotes (C$_1$–C$_8$)alkyl, (C$_2$–C$_8$)alkenyl, (C$_2$–C$_8$)-alkinyl, (C$_5$–C$_8$)cycloalkyl, phenyl or naphthyl, it being possible for the alkyl, alkenyl, alkinyl, cycloalkyl, phenyl or naphthyl radical to be monosubstituted or polysubstituted by halogen, (C$_1$–C$_4$)alkoxy, (C$_1$–C$_4$)alkyl, nitro, CF$_3$, nitrile, (C$_1$–C$_4$-alkoxy)-carbonyl, carbamyl which is optionally substituted by (C$_1$–C$_4$)alkyl and/or phenyl, (C$_1$–C$_6$-alkyl)-carbonyl, (C$_1$–C$_6$alkyl)-carbonylamino, benzoylamino or di-(C$_1$–C$_4$)-alkylamino, or by a phenyl or phenoxy radical each of which is optionally monosubstituted or polysubstituted by halogen, (C$_1$–C$_4$)alkoxy, (C$_1$–C$_4$)-alkyl, nitro, CF$_3$ or nitrile, or denotes (C$_1$–C$_4$-alkoxy)-carbonyl, or a carbamyl radical which is optionally substituted by (C$_1$–C$_4$)alkyl or phenyl, R$^2$ denotes (C$_1$–C$_4$)-alkyl, (C$_1$–C$_4$)-alkoxy or phenyl,
R$^3$ denotes (C$_1$–C$_4$)-alkyl,
R$^4$ denotes H or (C$_1$–C$_3$)-alkyl,
Ar denotes a phenyl, naphthyl or quinolyl radical, each of which can be mono-, di- or tri-substituted by halogen and/or mono- or di-substituted by CF$_3$, (C$_1$–C$_4$)-alkyl, (C$_1$–C$_4$)-alkoxy, CN, NO$_2$, (C$_1$–C$_6$-alkyl)-carbonyl or benzoyl, and
n denotes 1, 2, 3 or 4.

In the case of the radical Ar, halogen denotes, in particular, chlorine.

Preferred compounds of the formula I are those in which

R$^1$ denotes (C$_1$–C$_8$)alkyl or phenyl, each of which can be substituted as described above,
R$^2$ denotes (C$_1$–C$_4$)-alkoxy,
R$^4$ denotes H or methyl,
Ar denotes phenyl, which can be substituted by one to three halogen atoms, and
n denotes 1.

Examples of the compounds of the formula I which may be mentioned are: 3,4-dichlorophenoxyacetyloximino-phenylmethanephosphonic acid diethyl ester, 2,4-dichlorophenoxyacetyloximino-phenylmethanephosphonic acid diethyl ester, 4-chlorophenoxyacetyloximino-phenylmethanephosphonic acid diethyl ester, 3-chlorophenoxyacetyloximino-phenylmethanephosphonic acid diethyl ester, 4-chlorophenyl-3,4-dichlorophenoxyacetyloximino-methanephosphonic acid diethyl ester, 4-chlorophenyl-4-chlorophenoxyacetyloximino-methanephosphonic acid diethyl ester, 4-chlorophenyl-3-chlorophenoxyacetyloximino-methanephosphonic acid diethyl ester, 1-(2,4-dichlorophenoxyacetyloximino)-ethanephosphonic acid diethyl ester, 1-(3,4-dichlorophenoxyacetyloximino)-ethanephosphonic acid diethyl ester, 1-(4-chlorophenoxyacetyloximino)-ethanephosphonic acid diethyl ester, 1-(3-chlorophenoxyacetyloximino)-ethanephosphonic acid diethyl ester, 1-(2,4-dichlorophenoxyacetyloximino)-ethanephosphonic acid dimethyl ester, 3,4-dichlorophenoxyacetyloximino-3-phenoxyphenyl-methanephosphonic acid diethyl ester, 4-chlorophenoxyacetyloximino-3-phenoxyphenyl-methanephosphonic acid diethyl ester, 3-chlorophenoxyacetyoximino-3-phenoxyphenylmethanephosphonic acid diethyl ester, 2-chlorophenyl-3,4-dichlorophenoxyacetyloximino-methanephosphonic acid diethyl ester, 4-chlorophenoxyacetyloximino-4-methylphenylmethanephosphonic acid diethyl ester, 1-(4-chlorophenoxyacetyloximino)-hexanephosphonic acid diethyl ester, 1-(4-chlorophenoxyacetyloximino)-butanephosphonic acid diethyl ester, 1-(3-chlorophenoxyacetyloximino)-hexanephosphonic acid diethyl ester, 2-(4-chlorophenoxy)-propionyloximino-4-chlorophenyl-methanephosphonic acid diethyl ester, 1-[2-(4-chlorophenoxy)-propionyloximino]-ethanephosphonic acid diethyl ester and 1-[2-(4-chlorophenoxy)-propionyloximino]-hexanephosphonic acid diethyl ester.

The present invention also relates to a process for the preparation of the compounds of the general formula I, which comprises
(a) reacting a compound of the formula II $$R^1-\underset{\underset{NOH}{\overset{||}{C}}}{\overset{\overset{O}{\overset{||}{}}}{C}}-P\overset{\overset{O}{\overset{||}{\diagup}}R^2}{\diagdown OR^3} \quad (II)$$

with a compound of the formula III $$Ar-O-\left(\underset{R^4}{\overset{|}{C}H}\right)_n-COCl \quad (III)$$

in the presence of an auxiliary base, or
(b) reacting a compound of the formula II with a compound of the formula IV $$Ar-O-\left(\underset{R^4}{\overset{|}{C}H}\right)_n-CO_2H \quad (IV)$$

in the presence of a condensing agent.

The compounds of the formula II are known: J. Org. Chem. 33, 3090 (1968), British Pat. No. 1,207,788 and German Offenlegungsschrift No. 2,553,442.

Process variant (a) is advantageously carried out in an inert diluent, such as, for example, tetrahydrofuran, dioxane, acetonitrile, chloroform, toluene or dimethylformamide, at temperatures between 0° C. and 120° C., preferably between 20° C. and 80° C., in the presence of an auxiliary base.

Examples of suitable auxiliary bases are tertiary organic amines, such as triethylamine, tributylamine, N-methylmorpholine or pyridine, or alkali metal hydrides, such as sodium hydride, alkali metal alcoholates, such as sodium ethanolate, alkali metal carbonates, such as potassium carbonate, and alkali metal hydroxides, such as sodium hydroxide, which can be employed in powder form as a suspension in an inert diluent or dissolved in a two-phase system with a phase transfer catalyst, such as benzyltriethylammonium chloride.

The reactions according to variant (b) are carried out in an inert diluent, such as, for example, tetrahydrofuran, dioxane, methylene chloride, chloroform, dimethoxyethane, ethyl acetate or a mixture thereof, at temperatures between −30° C. and 50° C.

Ethyl chloroformate or a dialkylcarbodiimide, such as dicyclohexylcarbodiimide, can be employed as the condensing agent.

The oximes of the formula I according to the invention can exist in two stereoisomeric forms, namely in the syn- or anti-form. The present invention relates to both forms and to mixtures thereof. The isomers can be obtained from the stereoisomer mixture in the customary manner.

Surprisingly, it has been found that compounds of the formula I have the property of reducing or completely eliminating the phytotoxic side effects of plant protection agents, in particular of herbicides, when used in crops of useful plants. The agents according to the invention can be applied together with other herbicides, and are then capable of antagonizing and completely eliminating the harmful side effects of these herbicides, without influencing the activity of these herbicides against harmful plants. Such compounds which have the property of protecting crop plants from phytotoxic damage by herbicides are called "antidotes" or "safeners".

Oxime ethers and esters (German Offenlegungsschrift No. 2,808,317) and aryloxy-acetonitriles and -amide oximes (European Published Specification No. 31,958 = U.S. Pat. No. 4,414,020) are already known as safener compounds for herbicides. However, these have inadequate actions.

The field of use of conventional plant protection agents can be very considerably increased with the aid of the compounds according to the invention. The present invention therefore also relates to a method of protecting crop plants from the phytotoxic side effects of plant protection agents, in particular herbicides, which comprises treating the plants, plant seeds or areas to be cultivated with a compound of the formula I before, after or, preferably, at the same time as with the plant protection agent.

For use, the compounds of the formula I can be formulated with customary formulation auxiliaries to give dusting agents, wettable powders, dispersions, emulsifiable concentrates and the like, and these are either used as such (dusting agents and pellets) or dissolved or dispersed in a solvent (water) before use.

The present invention therefore also relates to plant protection agents containing the compounds of the formula I.

The agents can be used as wettable powders, emulsifiable concentrates, sprayable solutions, dusting agents, dressing agents, granules or microgranules in the customary formulations.

Wettable powders are understood as meaning products which are uniformly dispersible in water and which, alongside the active ingredient, in addition to a diluent or inert substance if appropriate, also contain wetting agents, for example polyoxyethylated alkylphenols, polyoxyethylated fatty alcohols and alkyl- or alkylphenylsulfonates, and dispersing agents, for example sodium lignin-sulfonate, sodium 2,2'-dinaphthylmethane-6,6'-disulfonate, sodium dibutylnaphthalenesulfonate or sodium oleyl-methyl-tauride. They are prepared in the customary manner, for example by grinding and mixing the components.

Emulsifiable concentrates can be prepared, for example, by dissolving the active ingredient in an inert organic solvent, for example butanol, cyclohexanone, dimethylformamide, xylene or higher-boiling aromatics or hydrocarbons, with the addition of one or more emulsifiers. In the case of liquid active ingredients, all or some of the solvent content may be dispensed with. Examples of emulsifiers which can be used are: calcium salts of alkylarylsulfonic acids, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyglycol ethers, sorbitan fatty acid esters, polyoxyethylene sorbitan fatty acid esters or polyoxyethylene sorbitol esters.

Dusting agents are obtained by grinding the active ingredient with finely divided solid substances, for example talc or naturally occurring clays, such as kaolin, bentonite, pyrophyllite or diatomaceous earth.

Granules can be prepared either by spraying the active ingredient onto an adsorbent granular inert material, or by applying active ingredient concentrates to the surface of carriers, such as sand or kaolinites, or a granular inert material, by means of binders, for example polyvinyl alcohol, sodium polyacrylate or mineral oils. It is also possible for suitable active ingredients to be granulated in the customary manner for the preparation of fertilizer granules—if desired as a mixture with fertilizers.

The active ingredient concentration in wettable powders is about 10 to 90% by weight; the remainder to make up to 100% by weight consists of the usual formulation constituents. The active ingredient concentration in emulsifiable concentrates can be about 10 to 80% by weight. Formulations which can be dusted usually contain 5 to 20% by weight of active ingredient, and solutions which can be sprayed contain about 1 to 20% by weight. The active ingredient content in granules depends partly on whether the active compound is present in liquid or solid form and on what granulation auxiliaries, fillers and the like are used.

In addition, the active ingredient formulations mentioned contain, if appropriate, the particular customary tackifiers, wetting agents, dispersing agents, emulsifiers, penetrating agents, solvents, fillers or carriers.

For use, the concentrates in the commercially available form are diluted, if appropriate, in the customary manner, for example by means of water in the case of wettable powders, emulsifiable concentrates, dispersions and in some cases also microgranules. Dust-like and granular formulations and solutions which can be sprayed are usually not additionally diluted with further inert substances before use.

Examples of herbicides of which the phytotoxic side effects can be reduced by means of compounds of the formula I are carbamates, thiolcarbamates, halogenoacetanilides, substituted phenoxy-, naphthoxy- and phenoxyphenoxy-carboxylic acid derivatives and heteroaryloxyphenoxycarboxylic acid derivatives, such as quinolyloxy-, quinoxalyloxy-, pyridyloxy-, benzoxazolyloxy-, benzothiazolyloxy-phenoxy-carboxylic acid esters, and furthermore dimedone oxime derivatives. Phenoxyphenoxy- and heteroaryloxyphenoxy-carboxylic acid esters are preferred here. Particularly suitable esters here are the lower alkyl, alkenyl and alkinyl esters.

The following herbicides may be mentioned as examples, without a limitation thereby being intended:

(A) Herbicides of the phenoxyphenoxy- and heteroaryloxyphenoxy-carboxylic acid ($C_1$–$C_4$)alkyl, ($C_2$–$C_4$)-alkenyl and ($C_3$–$C_4$)alkinyl ester type, such as methyl 2-(2,4-dichlorophenoxy)-phenoxy)-propionate, methyl 2-(4-(4-bromo-2-chlorophenoxy)-phenoxy)-propionate, methyl 2-(4-(4-trifluoromethylphenoxy)-phenoxy)-propionate, methyl 2-(4-(2-chloro-4-trifluoromethylphenoxy)-phenoxy)-propionate, methyl 2-(4-(2,4-dichlorobenzyl)-phenoxy)-propionate, ethyl 4-(4-(4-trifluoromethylphenoxy)-phenoxy)-pent-2-enoate, ethyl 2-(4-(3,5-dichloropyridyl-2-oxy)-phenoxy)-propionate, propargyl 2-(4-(3,5-dichloropyridyl-2-oxy)-phenoxy)-propionate, ethyl 2-(4-(6-chlorobenzoxazol-2-yl-oxy)-phenoxy)-propionate, ethyl 2-(4-(6-chlorobenzothiazol-2-yl-oxy)-phenoxy)-propionate, methyl 2-(4-(3-chloro-5-trifluoromethyl-2-pyridyloxy)-phenoxy)-propionate, butyl 2-(4-(5-trifluoromethyl-2-pyridyloxy)-phenoxy)-propionate, ethyl 2-(4-(6-chloro-2-quinoxalyloxy)-phenoxy)-propionate, ethyl 2-(4-(6-fluoro-2-quinoxalyloxy)-phenoxy)-propionate and ethyl 2-(4-(6-chloro-2-quinolyloxy)-phenoxy)-propionate.

(B) Chloroacetanilide herbicides, such as N-methoxymethyl-2,6-diethyl-chloroacetanilide, N-(3'-methoxyprop-2'-yl)-methyl-6-ethyl-chloroacetanilide and N-(3-methyl-1,2,4-oxdiazol-5-yl-methyl)-chloroacetic acid 2,6-dimethylanilide.

(C) Thiolcarbamates, such as S-ethyl N,N-dipropylthiocarbamate or S-ethyl N,N-diisobutylthiocarbamate, and (D) Dimedone derivatives, such as 2-(N-ethoxybutyrimidoyl)-5-(2-ethylthiopropyl)-3-hydroxy-2-cyclohexen-1-one, 2-(N-ethoxybutyrimidoyl)-5-(2-phenylthiopropyl)-3-hydroxy-2-cyclohexen-1-one or 2-(1-allyloxyiminobutyl)-4-methoxycarbonyl-5,5-dimethyl-3-oxocyclohexenol.

The ratio of antidote:herbicide can vary within wide limits in the range between 1:10 and 10:1, in particular between 2:1 and 1:10. The particular optimum amounts of herbicide and antidote depend on the type of herbicide used or on the antidote used, and on the nature of the plant crop to be treated, and can be determined from case to case by corresponding experiments.

The main fields of use for the application of the safeners are, above all, cereal crops (wheat, rye, barley and oats), rice, maize, sorghum and also cotton, sugar beet, sugar cane and soybean.

Depending on their properties, the safeners of the formula I can be used for pretreatment of the seed of the crop plant (seed dressing) or can be introduced into the seed furrows before sowing or applied together with the herbicide, before or after emergence of the plants. Pre-emergence treatment includes both the treatment of the area to be cultivated before sowing and the treatment of the sown areas to be cultivated on which there is as yet no growth. Joint use with the herbicide is preferred. Tank mixes or finished formulations can be employed for this, it being possible for the abovementioned formulation auxiliaries to be used.

The required application amounts of the compounds of the formula I can vary within wide limits, depending on the indication, and also vary as a function of external conditions, such as soil conditions and climate conditions. In general, however, they are between 0.01 and 10 kg of active ingredient/ha.

The following examples serve further to illustrate the invention.

A. FORMULATION EXAMPLES (a) An antidote concentrate which is readily emulsifiable in water is obtained from 25% by weight of a compound of the formula I, 10% by weight of cyclohexanone, 50% by weight of xylene, 8% by weight of calcium dodecylbenzenesulfonate, 4% by weight of ethoxylated castor oil (40 moles of ethylene oxide) and 3% by weight of ethoxylated nonylphenol (10 moles of ethylene oxide).

The active ingredient is dissolved in the stated amounts of solvent, with stirring and gentle warming, and the emulsifiers are then added. The mixture is subsequently stirred at slightly elevated temperatures until the solution is clear and free from streaks.

(b) A concentrate of a phenoxycarboxylic acid ester and an antidote (10:1) which is readily emulsifiable in water is obtained from 12.00% by weight of ethyl 2-[4-(6-chlorobenzoxazol-2-yl-oxy)-phenoxy]-propionate, 1.20% by weight of a compound of the formula I, 69.00% by weight of xylene, 7.80% by weight of calcium dodecylbenzenesulfonate, 6.00% by weight of ethoxylated nonylphenol (10 moles of ethylene oxide) and 4.00% by weight of ethoxylated castor oil (40 moles of ethylene oxide).

The formulation is prepared as described under Example (a).

(c) A concentrate of a phenoxycarboxylic acid ester and an antidote (1:10) which is readily emulsifiable in water is obtained from 4.0% by weight of ethyl 2-[4-(6-chlorobenzoxazol-2-yl-oxy)-phenoxy]-propionate, 40.0% by weight of a compound of the formula I, 30.0% by weight of xylene, 20.0% by weight of cyclohexanone, 4.0% by weight of calcium dodecylbenzenesulfonate and 2.0% by weight of ethoxylated castor oil (40 moles of ethylene oxide).

The formulation is prepared as described under Example (a).

B. CHEMICAL EXAMPLES

EXAMPLE 1

4-Chlorophenoxyacetyloximino-4-chlorophenyl-methanephosphonic acid diethyl ester 12.3 g (0.06 mole) of 4-chlorophenoxyacetyl chloride, dissolved in 20 ml of toluene, were added dropwise to a solution of 17.5 g (0.06 mole) of 4-chlorophenylhydroximino-methanephosphonic acid diethyl ester and 7.2 g (0.072 mole) of triethylamine in 100 ml of toluene with stirring, the temperature being kept at a maximum of 35° C. by occasional cooling. The mixture was stirred at 60°–65° C. for 7 hours and cooled, the triethylamine hydrochloride which had precipitated out was filtered off with suction and the toluene phase was washed with water.

After drying with $Na_2SO_4$, the solvent was removed on a rotary evaporator and the residue was recrystallized from n-hexane/diisopropyl ether (1:1). 25.6 g (92.8%) of 4-chlorophenoxyacetyl-4-chlorophenylmethanephosphonic acid diethyl ester of melting point 67°–70° C. were obtained.

EXAMPLE 2

1-[2-(4-Chlorophenoxy)propionyloximino]-hexanephosphonic acid diethyl ester 8.8 g (0.04 mole) of 2-(4-chlorophenoxy)-propionyl chloride, dissolved in 20 ml of toluene, were added dropwise to a solution of 10.0 g (0.04 mole) of 1-hydroximinohexanephosphonic acid diethyl ester and 5.0 g (0.05 mole) of triethylamine in 80 ml of toluene. The mixture was subsequently stirred at 55° C. for 9 hours and cooled, the triethylamine hydrochloride which had precipitated was filtered off with suction and the organic phase was washed with water. After drying with $Na_2SO_4$, evaporating off the toluene on a rotary evaporator and removing, under a high vacuum, the solvent which still adhered, 13.8 g (77.8%) of 1-[2-(4-chlorophenoxy)-propionyloximino]-hexanephosphonic acid diethyl ester of $n_D^{22}=1.4919$ were obtained.

The compounds of the formula I listed below in Table 1 were obtained in an analogous manner.

TABLE 1

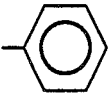
(I)

| Example No. | $R^1$ | $R^2$ | $R^3$ | $R^4$ | $R^5$ | $R^6$ | n | Melting point, $n_D^{20}$ |
|---|---|---|---|---|---|---|---|---|
| 3 | 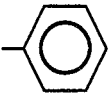 | $-OC_2H_5$ | $-C_2H_5$ | H | 4-Cl | H | 1 | 1.5504 |
| 4 | 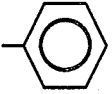 | $-OC_2H_5$ | $-C_2H_5$ | H | 2-Cl | 4-Cl | 1 | 1.5565 |
| 5 | 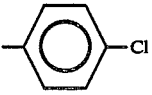 | $-OC_2H_5$ | $-C_2H_5$ | H | 3-Cl | 4-Cl | 1 | 1.5558 |
| 6 | 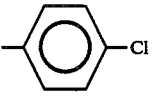 | $-OC_2H_5$ | $-C_2H_5$ | H | 3-Cl | H | 1 | 1.5565 |
| 7 | 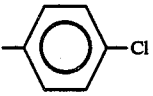 | $-OC_2H_5$ | $-C_2H_5$ | H | 2-Cl | 4-Cl | 1 | 1.5629 |
| 8 | 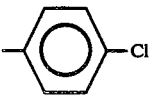 | $-OCH_3$ | $-CH_3$ | H | 2-Cl | 4-Cl | 1 | Oil |
| 9 | 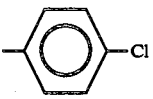 | $-OC_2H_5$ | $-C_2H_5$ | H | 3-Cl | 4-Cl | 1 | 1.5615 |
| 10 | 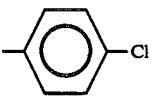 | $-OC_2H_5$ | $-C_2H_5$ | H | 4-$CH_3$ | H | 1 | 1.5483 |
| 11 | 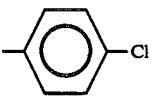 | $-OC_2H_5$ | $-C_2H_5$ | H | 2-$CH_3$ | 4-Cl | 1 | 1.5549 |

TABLE 1-continued
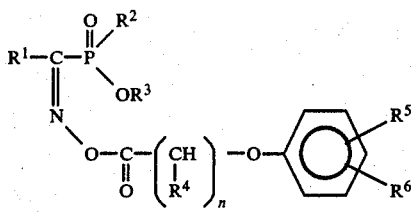
| Example No. | R¹ | R² | R³ | R⁴ | R⁵ | R⁶ | n | Melting point, $n_D^{20}$ |
|---|---|---|---|---|---|---|---|---|
| 12 | 4-Cl-C₆H₄- | —OC₂H₅ | —C₂H₅ | —CH₃ | 4-Cl | H | 1 | 1.5203 |
| 13 | 4-Cl-C₆H₄- | —OC₂H₅ | —C₂H₅ | H | 4-Cl | H | 3 | Oil |
| 14 | 3-Cl-C₆H₄- | —OC₂H₅ | —C₂H₅ | H | 4-Cl | H | 1 | Oil |
| 15 | 3-Cl-C₆H₄- | —OC₂H₅ | —C₂H₅ | —CH₃ | 4-Cl | H | 1 | Oil |
| 16 | 3-Cl-C₆H₄- | —OC₂H₅ | —C₂H₅ | H | 4-Cl | H | 3 | Oil |
| 17 | 2-Cl-C₆H₄- | —OC₂H₅ | —C₂H₅ | H | 4-Cl | H | 1 | 1.5519 |
| 18 | 2-Cl-C₆H₄- | —OC₂H₅ | —C₂H₅ | H | 3-Cl | H | 1 | 1.5529 |
| 19 | 2-Cl-C₆H₄- | —OC₂H₅ | —C₂H₅ | H | 3-Cl | 4-Cl | 1 | 1.5585 |
| 20 | 2-Cl-C₆H₄- | —CH₃ | —C₂H₅ | H | 3-Cl | 4-Cl | 1 | Oil |

TABLE 1-continued $$\underset{\substack{\text{R}^1-\text{C}-\text{P} \\ \parallel \\ \text{N} \\ \text{O}-\text{C}-(\text{CH})_n-\text{O}-\text{C}_6\text{H}_3(\text{R}^5)(\text{R}^6) \\ \parallel \\ \text{O} \quad \text{R}^4}}{\overset{\text{O} \quad \text{R}^2}{\underset{\text{OR}^3}{}}}$$ (I)

| Example No. | R¹ | R² | R³ | R⁴ | R⁵ | R⁶ | n | Melting point, $n_D^{20}$ |
|---|---|---|---|---|---|---|---|---|
| 21 | 2-Cl-C₆H₄ | —OC₂H₅ | —C₂H₅ | —CH₃ | 4-Cl | H | 1 | 1.5781 |
| 22 | 4-CH₃-C₆H₄ | —OC₂H₅ | —C₂H₅ | H | 4-Cl | H | 1 | 1.5521 |
| 23 | 4-CH₃-C₆H₄ | —OC₂H₅ | —C₂H₅ | H | 3-Cl | H | 1 | 1.5515 |
| 24 | 4-CH₃-C₆H₄ | —CH₃ | —C₂H₅ | H | 3-Cl | H | 1 | Oil |
| 25 | 4-CH₃-C₆H₄ | —OC₂H₅ | —C₂H₅ | H | 3-Cl | 4-Cl | 1 | 1.5583 |
| 26 | 4-CH₃-C₆H₄ | —OC₂H₅ | —C₂H₅ | H | 4-CH₃ | H | 1 | 1.5440 |
| 27 | 4-CH₃-C₆H₄ | —OC₂H₅ | —C₂H₅ | H | 4-Cl | 2-CH₃ | 1 | 1.5499 |
| 28 | 4-CH₃-C₆H₄ | —OC₂H₅ | —C₂H₅ | —CH₃ | 4-Cl | H | 1 | 1.5103 |
| 29 | 4-OCH₃-C₆H₄ | —OC₂H₅ | —C₂H₅ | H | 4-Cl | H | 1 | 1.5595 |
| 30 | 4-OCH₃-C₆H₄ | —OC₂H₅ | —C₂H₅ | H | 3-Cl | H | 1 | 1.5605 |
| 31 | 4-OCH₃-C₆H₄ | —OC₂H₅ | —C₂H₅ | H | 3-Cl | 4-Cl | 1 | 1.5659 |

TABLE 1-continued $$\underset{\underset{O}{\overset{R^1-C}{\|}}}{\overset{\overset{O}{\|}}{P}}\underset{OR^3}{\overset{R^2}{\|}}$$
$$\|$$
$$N-O-\underset{\underset{O}{\|}}{C}-(\underset{R^4}{\overset{CH}{\|}})_n-O-\text{Ar}(R^5)(R^6)$$

(I)

| Example No. | R¹ | R² | R³ | R⁴ | R⁵ | R⁶ | n | Melting point, $n_D^{20}$ |
|---|---|---|---|---|---|---|---|---|
| 32 | 4-methoxyphenyl | —OC$_2$H$_5$ | —C$_2$H$_5$ | —CH$_3$ | 4-Cl | H | 1 | 1.5009 |
| 33 | 4-methoxyphenyl | —OCH$_3$ | —CH$_3$ | —CH$_3$ | 4-Cl | H | 1 | Oil |
| 34 | 3-phenoxyphenyl | —OC$_2$H$_5$ | —C$_2$H$_5$ | H | 4-Cl | H | 1 | 1.5684 |
| 35 | 3-phenoxyphenyl | —OC$_2$H$_5$ | —C$_2$H$_5$ | H | 3-Cl | H | 1 | Oil |
| 36 | 3-phenoxyphenyl | —OC$_2$H$_5$ | —C$_2$H$_5$ | H | 3-Cl | 4-Cl | 1 | Oil |
| 37 | 3-phenoxyphenyl | —OC$_2$H$_5$ | —C$_2$H$_5$ | —CH$_3$ | 4-Cl | H | 1 | 1.5958 |
| 38 | cyclohexyl | —OC$_2$H$_5$ | —C$_2$H$_5$ | —CH$_3$ | 4-Cl | H | 1 | 1.6024 |
| 39 | cyclohexyl | —OC$_2$H$_5$ | —C$_2$H$_5$ | H | 3-Cl | H | 1 | 48° C. |
| 40 | —CH$_3$ | —OC$_2$H$_5$ | —C$_2$H$_5$ | H | 4-Cl | H | 1 | 1.5145 |
| 41 | —CH$_3$ | —OC$_2$H$_5$ | —C$_2$H$_5$ | H | 4-Cl | H | 3 | Oil |
| 42 | —CH$_3$ | —OC$_2$H$_5$ | —C$_2$H$_5$ | H | 2-Cl | 4-Cl | 1 | 95–97° C. |
| 43 | —CH$_3$ | —OC$_2$H$_5$ | —C$_2$H$_5$ | H | 3-Cl | 4-Cl | 1 | 1.5245 |
| 44 | —CH$_3$ | —OC$_2$H$_5$ | —C$_2$H$_5$ | H | 3-Cl | H | 1 | 1.5138 |
| 45 | —CH$_3$ | —OC$_2$H$_5$ | —C$_2$H$_5$ | —CH$_3$ | 4-Cl | H | 1 | 1.4793 |

TABLE 1-continued $$R^1-C(=N-O-C(=O)-(CH(R^4))_n-O-\text{Ar}(R^5)(R^6))-P(=O)(R^2)(OR^3) \quad (I)$$

| Example No. | $R^1$ | $R^2$ | $R^3$ | $R^4$ | $R^5$ | $R^6$ | n | Melting point, $n_D^{20}$ |
|---|---|---|---|---|---|---|---|---|
| 46 | —$C_2H_5$ | —$OC_2H_5$ | —$C_2H_5$ | H | 4-Cl | H | 1 | 1.5151 |
| 47 | —$C_2H_5$ | —$OC_2H_5$ | —$C_2H_5$ | H | 3-Cl | H | 1 | 1.5155 |
| 48 | —$C_2H_5$ | —$OC_2H_5$ | —$C_2H_5$ | —$CH_3$ | 4-Cl | H | 1 | 1.5204 |
| 49 | —$C_2H_5$ | —$OC_2H_5$ | —$C_2H_5$ | H | 3-Cl | 4-Cl | 1 | 1.5243 |
| 50 | —$CH(CH_3)_2$ | —$OC_2H_5$ | —$C_2H_5$ | H | 4-Cl | H | 1 | 1.5118 |
| 51 | —$CH(CH_3)_2$ | —$OC_2H_5$ | —$C_2H_5$ | H | 4-$CH_3$ | H | 1 | 1.5842 |
| 52 | —$CH(CH_3)_2$ | —$OC_2H_5$ | —$C_2H_5$ | —$CH_3$ | 4-Cl | H | 1 | 1.5406 |
| 53 | —$C_5H_{11}$ | —$OC_2H_5$ | —$C_2H_5$ | H | 4-$CH_3$ | H | 1 | 1.5842 |
| 54 | —$C_5H_{11}$ | —$OC_2H_5$ | —$C_2H_5$ | H | 4-Cl | H | 1 | 1.5835 |
| 55 | —$C_5H_{11}$ | —$OC_2H_5$ | —$C_2H_5$ | H | 3-Cl | H | 1 | 1.5800 |
| 56 | —C(=O)—N($CH_3$)—Ph | —$OC_2H_5$ | —$C_2H_5$ | H | 4-Cl | H | 1 | 117° C. |
| 57 | —C(=O)—N($CH_3$)—Ph | —$OC_2H_5$ | —$C_2H_5$ | H | 2-Cl | 4-Cl | 1 | 1.5485 |
| 58 | —C(=O)—N($CH_3$)—Ph | —$OC_2H_5$ | —$C_2H_5$ | H | 2-$CH_3$ | 4-Cl | 1 | 96–98° C. |

C. BIOLOGICAL EXAMPLES

EXAMPLE 1

Wheat was grown to the 3–4 leaf stage in a greenhouse in pots of 9 cm φ and then treated with the herbicide and the compounds according to the invention. The compounds were applied in the form of aqueous suspensions or emulsions in the form of a tank mix, the amount of water applied, when converted, being 800 l/ha. 3 weeks after the treatment, the plants were evaluated for any type of damage by the herbicides applied, the degree of lasting inhibition of growth particularly being taken into consideration.

The results from Table 1 illustrate the high antidote action of the compounds according to the invention.

TABLE 1

| Herbicide/antidote combination | Dose kg of a.i./ha | Herbicidal action in % TA |
|---|---|---|
| $H_1$ | 2 | 80 |
| $H_1$ + compound from Example 34 | 2 + 2.5 | 20 |
| $H_1$ + compound from Example 1 | 2 + 2.5 | 22 |
| $H_1$ + compound from Example 5 | 2 + 2.5 | 30 |
| $H_1$ + compound from Example 3 | 2 + 2.5 | 40 |
| $H_1$ + compound from Example 43 | 2 + 2.5 | 35 |
| $H_1$ + compound from Example 4 | 2 + 2.5 | 40 |
| $H_1$ + compound from Example 10 | 2 + 2.5 | 55 |
| $H_1$ + compound from Example 9 | 2 + 2.5 | 20 |

TABLE 1-continued

| Herbicide/antidote combination | Dose kg of a.i./ha | Herbicidal action in % TA |
|---|---|---|
| $H_1$ + compound from Example 7 | 2 + 2.5 | 65 |
| $H_1$ + compound from Example 6 | 2 + 2.5 | 45 |
| $H_1$ + compound from Example 25 | 2 + 2.5 | 30 |
| $H_1$ + compound from Example 29 | 2 + 2.5 | 30 |
| $H_1$ + compound from Example 23 | 2 + 2.5 | 30 |
| $H_1$ + compound from Example 22 | 2 + 2.5 | 25 |
| $H_1$ + compound from Example 19 | 2 + 2.5 | 40 |
| $H_1$ + compound from Example 17 | 2 + 2.5 | 30 |
| $H_1$ + compound from Example 11 | 2 + 2.5 | 55 |
| $H_1$ + compound from Example 46 | 2 + 2.5 | 40 |
| $H_1$ + compound from Example 31 | 2 + 2.5 | 30 |
| $H_1$ + compound from Example 30 | 2 + 2.5 | 40 |
| $H_1$ + compound from Example 14 | 2 + 2.5 | 40 |
| $H_1$ + compound from Example 2 | 2 + 2.5 | 50 |
| $H_1$ + compound from Example 51 | 2 + 2.5 | 60 |
| $H_1$ + compound from Example 49 | 2 + 2.5 | 40 |
| $H_1$ + compound from Example 35 | 2 + 2.5 | 60 |
| $H_1$ + compound from Example 39 | 2 + 2.5 | 50 |
| $H_1$ + compound from Example 36 | 2 + 2.5 | 40 |
| $H_1$ + compound from Example 12 | 2 + 2.5 | 50 |
| $H_1$ + compound from Example 21 | 2 + 2.5 | 60 |
| $H_1$ + compound from Example 55 | 2 + 2.5 | 65 |
| $H_1$ + compound from Example 54 | 2 + 2.5 | 40 |
| $H_1$ + compound from Example 32 | 2 + 2.5 | 45 |
| $H_1$ + compound from Example 45 | 2 + 2.5 | 55 |

TABLE 1-continued

| Herbicide/antidote combination | Dose kg of a.i./ha | Herbicidal action in % TA |
|---|---|---|
| H₁ + compound from Example 44 | 2 + 2.5 | 45 |

Abbreviations:
H₁ = fenoxaprop-ethyl = (ethyl 2-[4-(6-chlorobenzoxazol-2-yl-oxy)-phenoxy]-propionate)
TA = *Triticum aestivum*
a.i. = active ingredient

EXAMPLE 2

Maize plants were grown as in Example 1 and were treated with the herbicide and the compounds according to the invention as described above. After 3 weeks, damage to the maize plants was evaluated visually.

The results of the evaluation are summarized in Table 2. The compounds according to the invention are accordingly capable of effectively reducing damage caused by use of herbicides.

TABLE 2

| Herbicide/antidote combination | Dose kg of a.i./ha | Herbicidal action in % ZM |
|---|---|---|
| H₂ | 0.4 | 95 |
| H₂ + compound from Example 1 | 0.4 + 2.5 | 35 |
| H₂ + compound from Example 5 | 0.4 + 2.5 | 70 |
| H₂ + compound from Example 3 | 0.4 + 2.5 | 60 |
| H₂ + compound from Example 43 | 0.4 + 2.5 | 40 |
| H₂ + compound from Example 40 | 0.4 + 2.5 | 20 |
| H₂ + compound from Example 9 | 0.4 + 2.5 | 40 |
| H₂ + compound from Example 6 | 0.4 + 2.5 | 40 |
| H₂ + compound from Example 25 | 0.4 + 2.5 | 60 |
| H₂ + compound from Example 29 | 0.4 + 2.5 | 30 |
| H₂ + compound from Example 22 | 0.4 + 2.5 | 35 |
| H₂ + compound from Example 19 | 0.4 + 2.5 | 60 |
| H₂ + compound from Example 18 | 0.4 + 2.5 | 50 |
| H₂ + compound from Example 17 | 0.4 + 2.5 | 25 |
| H₂ + compound from Example 11 | 0.4 + 2.5 | 50 |
| H₂ + compound from Example 46 | 0.4 + 2.5 | 20 |
| H₂ + compound from Example 31 | 0.4 + 2.5 | 40 |
| H₂ + compound from Example 30 | 0.4 + 2.5 | 40 |
| H₂ + compound from Example 14 | 0.4 + 2.5 | 35 |
| H₂ + compound from Example 47 | 0.4 + 2.5 | 60 |
| H₂ + compound from Example 28 | 0.4 + 2.5 | 50 |
| H₂ + compound from Example 37 | 0.4 + 2.5 | 35 |
| H₂ + compound from Example 48 | 0.4 + 2.5 | 60 |
| H₂ + compound from Example 36 | 0.4 + 2.5 | 40 |
| H₂ + compound from Example 50 | 0.4 + 2.5 | 30 |

Abbreviations:
H₂ = diclofopmethyl (methyl 2-[4-(2,4-dichlorophenoxy)-phenoxy]-propionate)
ZM = *Zea mays*

We claim:

1. A compound of the formula I

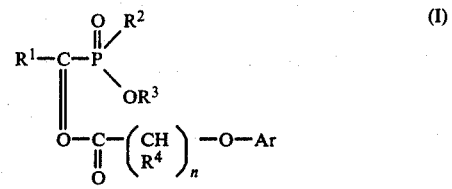

in which
R¹ is (C₁-C₈)alkyl, (C₅-C₈)cycloalkyl, phenyl or naphthyl, it being possible for the alkyl, cycloalkyl, phenyl or naphthyl radical to be monosubstituted by halogen, (C₁-C₄)alkoxy, (C₁-C₄)alkyl, nitro, CF₃, nitrile, (C₁-C₄-alkoxy)-carbonyl, (C₁-C₆alkyl)-carbonylamino, benzoylamino, phenyl or a phenoxy radical or is (C₁-C₄-alkoxy)-carbonyl, or a carbamyl radical which is unsubstituted or substituted by (C₁-C₄)alkyl or phenyl,
R² is (C₁-C₄)alkyl, (C₁-C₄)-alkoxy or phenyl,
R³ is (C₁-C₄)alkyl,
R⁴ is H or (C₁-C₃)-alkyl,
Ar is a phenyl radical, which can be mono-, di- or tri-substituted by halogen and/or mono- or di-substituted by CF₃, (C₁-C₄)-alkyl, (C₁-C₄)-alkoxy, CN, NO₂ or (C₁-C₆-aklyl)-carbonyl and
n is 1 or 3.

2. A compound of the formula I

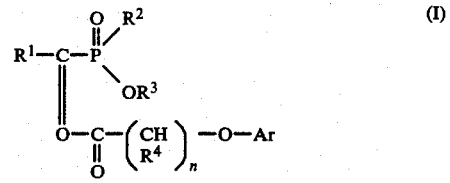

in which
R¹ is (C₁-C₈)alkyl, (C₅-C₈)cycloalkyl, or phenyl, it being possible for the phenyl radical to be monosubstituted by halogen, (C₁-C₄)alkoxy, (C₁-C₄)-alkyl or by a phenoxy radical, or is a carbamoyl radical which is substituted by (C₁-C₄)-alkyl or phenyl,
R² is (C₁-C₄)alkyl or (C₁-C₄)alkoxy,
R³ is (C₁-C₄)alkyl,
R⁴ is H or (C₁-C₃)alkyl,
Ar is a phenyl radical which can be mono- or di-substituted by halogen and/or (C₁-C₄)alkyl, and
n is 1 or 3.

3. A compound of the formula I as claimed in claim 2 in which
R¹ is (C₁-C₅)alkyl, cyclohexyl, or phenyl, it being possible for the phenyl radical to be monosubstituted by halogen, (C₁-C₃)alkoxy or phenoxy,
R² is (C₁-C₃)alkoxy,
R³ is (C₁-C₃)alkyl,
R⁴ is H or (C₁-C₂)alkyl
Ar is phenyl which can be mono- or di-substituted by halogen or (C₁-C₂)aklyl, and
n is 1.

* * * * *